United States Patent [19]

Jakubowycz

[11] Patent Number: 5,571,938
[45] Date of Patent: Nov. 5, 1996

[54] ESTERIFICATION PROCESS USING A CATALYST CONSISTING OF SAND, STANNOUS TIN AND ALUMINATE

[76] Inventor: Stan Jakubowycz, 504 Albermarle Rd., Bricktownship, Ocean Co., N.J. 08724

[21] Appl. No.: 509,609

[22] Filed: Jul. 31, 1995

Related U.S. Application Data

[62] Division of Ser. No. 172,703, Dec. 27, 1993, Pat. No. 5,462,906.

[51] Int. Cl.$^6$ .................................................. C07C 67/00
[52] U.S. Cl. ........................ 560/204; 560/99; 554/121; 554/170
[58] Field of Search ................ 560/99, 204; 554/121, 554/167, 170

[56] References Cited

U.S. PATENT DOCUMENTS

| | | |
|---|---|---|
| 2,411,136 | 11/1946 | Luce . |
| 3,260,677 | 7/1966 | Riley et al. . |
| 3,907,709 | 9/1975 | List et al. ............................. 252/453 |
| 4,374,263 | 2/1983 | Hancock et al. . |
| 4,507,410 | 3/1985 | Falardeau et al. . |
| 4,675,434 | 6/1987 | Uhm et al. . |
| 5,137,863 | 8/1992 | Matsuura et al. . |
| 5,462,906 | 10/1995 | Jakubowycz . |

*Primary Examiner*—Samuel Barts
*Attorney, Agent, or Firm*—Roylance, Abrams, Berdo & Goodman, L.L.P.

[57] ABSTRACT

The present invention provides for an esterification process comprising a catalyst source of stannous tin and an alkali metal aluminate. In one preferred embodiment the catalyst comprises about 92 parts sand, about 5 parts stannous oxalate, and about 3 parts of a sodium aluminate, by weight, dry basis. This catalyst is particularly useful in making phthalates, adipates, sebacates and azelates which esters are chiefly used plasticizers.

7 Claims, No Drawings

ESTERIFICATION PROCESS USING A CATALYST CONSISTING OF SAND, STANNOUS TIN AND ALUMINATE

This is a division of application Ser. No. 08/172,703 filed Dec. 27, 1993, now U.S. Pat. No. 5,462,906.

FIELD OF THE INVENTION

The present invention relates to esterification catalysts and to a process for the production of esters by the reaction of aliphatic alcohols, aromatic alcohols, or glycols with organic acids, organic acid anhydrides, organic diacids or their methyl or ethyl esters, and monobasic organic acids, in the presence of the catalyst of the invention. In particular, the invention relates to the production of high-boiling esters such as phthalates, adipates, sebacates, and azelates, which are chiefly used as plasticizers and/or synthetic lubricants.

BACKGROUND OF THE INVENTION

Over the years a variety of catalysts have been employed in the production of high-boiling esters. Strong mineral acids, such as sulphuric acid and phosphoric acid, and organic acids such as para-toluene sulphonic acid, have been used extensively. Notwithstanding their extensive use, it has long been recognized that there are problems associated with the use of these catalysts.

In order to achieve commercially viable production rates at temperatures low enough to produce commercially acceptable products, it is necessary to employ such high acid concentrations that these concentrations often cause dehydration of the alcohol reactant. This gives rise to the production of unwanted olefins and ethers, discoloration of the ester product, and an extensive washing step at the end to remove the residual acidity.

Problems caused by the use of strong acid catalysts are known to be alleviated to a great extent by the use of amphoteric catalysts instead of strong acid catalysts. Amphoteric catalysts may be described as compounds of elements capable of functioning as both cations and anions.

The catalyst of the present invention, in a preferred embodiment, comprises a mixture of stannous oxalate and a sodium aluminate in a carrier such as sand. It should be noted that silica sand, ordinarily made up of negatively charged particles, is capable of transporting metallic ions.

In the prior art, it has been known to use stannous oxalate as an active catalytic ingredient to catalyze an esterification reaction. British patent publication GB 990,927 discloses catalysts wherein the active ingredient is a stannous salt of a carboxylic acid.

Also it has been known to use a sodium aluminate as the active ingredient to catalyze esterification reactions. U.S. Pat. No. 3,907,709 of List et al. describes silica-gel catalysts which comprise as the active ingredient a sodium compound, or an aluminum compound, or a tin compound. In their example, List et al. describe silica gel (the carrier) impregnated with a sodium aluminate (the active catalytic material).

However, up until now, it has not been known to use a catalyst which comprises a blend of the two active ingredients, stannous oxalate and a sodium aluminate in an inert carrier.

SUMMARY OF THE INVENTION

The present invention in one embodiment comprises a catalyst suitable for the production of high boiling esters, comprising a mixture of tin salt, and an aluminate, wherein the tin salt is capable of reacting with the aluminum salt to form stannous aluminate or provide a stannous ion. In another embodiment, the catalyst comprises a mixture of stannous salt, aluminate and finely divided sand.

In yet another embodiment, the invention comprises a catalyst suitable for the production of high boiling esters comprising a mixture of stannous oxalate and a sodium aluminate, or alternately comprises stannous oxalate, sodium aluminate, and finely divided sand.

In still another embodiment, the invention comprises a process for making high boiling esters comprising the step of reacting alcohol with a carboxylic acid or a carboxylic acid anhydride in the presence of an esterification catalyst consisting essentially of about 1%–92% by weight of a carrier such as sand; and 99%–8% by weight of a mixture of stannous oxalate and sodium aluminate. The mixture should contain at least 1% by weight stannous oxalate and at least 1% by weight sodium aluminate, dry basis.

DETAILED DESCRIPTION OF THE INVENTION IN GENERAL

The technology of the invention is esterification. The preferred alcohols to use include: 2-ethyl hexanol; normal hexanol; tridecanol; isodecanol; other $C_4$ to $C_{15}$ alcohols, and equivalent glycols having carbon atoms within the same range as the alcohols, or glycol ethers (i.e., $C_4$ to $C_{15}$). The preferred organic acids to use include: phthalic anhydride; adipic acid; sebacic acid; azelaic acid; trimelletic acid or anhydride; monobasic acids, such as heptanoic acid; and any $C_4$ to $C_{15}$ diacid, or $C_4$ to $C_{15}$ monobasic acid or the methyl ester or diester, of any of these acids. In other words, the preferred acid component may be used either in the acid form, as the anhydride, or as the methyl or dimethyl ester.

The reaction is preferably carried out by first adding the alcohol to an empty reactor since all the preferred alcohols are liquids, then mixing the catalyst with the alcohol, and finally, adding one of the preferred acids or acid anhydrides, all of which are solids. The reaction is subsequently carried out, preferably under vacuum, in the temperature range of 215° C. or more, in the presence of the catalyst. The novelty is in the use of a catalyst that comprises both a tin salt and an aluminate preferably in an inert carrier.

In one embodiment, the catalyst has three components and is made up of fine silicon dioxide (sand), sodium aluminate, and stannous oxalate. The sand is of very fine particle sizes, with diameters in the range of from about predominantly 5 microns to about predominantly 325 microns, or preferably, in the range of from about predominantly 5 microns to about predominantly 50 microns. The sand acts as an inert carrier for the two other ingredients. Generally, the sand makes up about 1% to 92% by weight of the catalyst composition on a dry basis, and the mixture of the two active catalytic components may be up to about 99% by weight of the catalyst composition.

After the alcohol, acid, and the novel catalyst have been placed in the reactor, the manhole of the reactor is closed. The reaction is then carried out, preferably under vacuum, and at an elevated temperature, to produce the desired ester.

It is contemplated that the tin source may be selected from a group which includes not only stannous oxalates but also dibutyl tin oxide, and other tin compounds that are capable of reacting with a sodium aluminate or other aluminate salts to form stannous aluminate. It is further contemplated that the aluminate may be selected from the group that includes not only a sodium aluminate, but also other alkali metal aluminates, such as potassium, magnesium, or cesium aluminates.

A range of amounts (proportions) of sodium aluminate and stannous oxalate can be used in the catalyst composition, although good results were found using 3% sodium aluminate and 5% stannous oxalate, based on the three component composition including sand. Applicants have determined that the amount of sodium aluminate should be at least about 1% and the amount of stannous oxalate should be at least 1%, both by weight based on the catalytic 3-component composition. Good results were obtained when the ratio of sodium aluminate to stannous oxalate was 3:5 and when the ratio was 25:5. It has been concluded that best results are obtained if a preponderance of sodium aluminate is used and if a preponderance of stannous oxalate is used.

In broad terms, the present invention is a process for the production of esters boiling above 100° C., which process comprises reacting an alcohol with a carboxylic acid or a carboxylic acid anhydride, preferably under vacuum, at a temperature greater than 160° C., in the presence of an esterification catalyst of the invention.

The process of the invention is generally applicable to the production of esters which boil above 100° C. at atmospheric pressure. Preferably the esterification reaction temperature is in the range from 180° C. to 225° C. The temperature may suitably be controlled by the addition of an inert diluent of appropriate boiling point.

The Reactants

It is contemplated that the process is applicable to the production of esters derived from any of the following acids:

monobasic aliphatic carboxylic acids—containing up to 20 carbon atoms, e.g., alkanoic acids such as myristic, palmitic and stearic acid, alkenoic acids such as oleic acid or derivatives of such alkanoic and alkenoic acids, e.g., ricinoleic acid;

aliphatic dibasic carboxylic acids—especially those containing up to 20 carbon atoms, preferably up to 10 carbon atoms as for example adipic, azelaic or sebacic acid;

tribasic aliphatic acids—such as citric acid;

monobasic aromatic acids—suitably those containing up to 10 carbon atoms, such as benzoic acid;

dibasic aromatic acids and their anhydrides—such as the three phthalic acids, especially phthalic acid itself (ortho-phthalic acid) or phthalic anhydride, and their hydrogenration products, e.g., hexahydrophthalic anhydride; and tribasic aromatic acids and their anhydrides—such as hemimellitic, trimellitic, or trimesic acids and their anhydrides.

The more preferred acids are ortho-phthalic acid or its anhydride, adipic acid, azelaic acid, and sebacic acid.

The process of the invention is particularly applicable to esters derived from any of the following alcohols:

monohydric alcohols—containing up to 20 carbon atoms, particularly alkanols containing from 4 to 14 carbon atoms, e.g., butanol, isoheptanol, iso-octanol, 2-ethylhexanol, nonanol, decanol, tridecanol, and mixtures of alcohols containing, for example, 7 to 9 carbon atoms such as are obtained from olefinic mixtures by the OXO process;

dihydric alcohols—containing up to 20 carbon atoms, e.g., ethylene glycol, diethylene glycol, triethylene glycol, mono-, di- or tripropylene glycol, the butylene glycols, and 2,2,4-tri-methylpentane diol;

trihydric alcohols—such as glycerol;

aliphatic cyclic alcohols—containing up to 12 carbon atoms, such as cyclohexanol; and derivatives—particularly other derivatives of the dihydric and trihydric alcohols, e.g., lower alkyl ether derivatives, such as 2-butoxy ethanol.

The preferred alcohols are the monohydric alcohols containing 4 to 14 carbon atoms.

It is contemplated that the stannous salts suitable for use as the tin component of the catalyst may be salts of acids which are saturated, aliphatic or aromatic, mono-, di- or polycarboxylic. Thus, suitable catalysts include stannous acetate, stannous tartrate, stannous benzoate, stannous citrate, stannous oxalate, stannous phthalate, stannous sebacate, stannous formate and stannous octoate. More preferably, however, the salts are of acids containing at most 7 carbon atoms.

It is contemplated that the aluminates that are suitable for use as a component of the catalyst are those that are highly soluble in water. Suitable aluminates include sodium aluminate, potassium aluminate, magnesium aluminate, cesium aluminate and mixtures thereof.

It is contemplated that the finely divided sands useful as the sand component of the catalyst include silica sand, quartz sand, chromite sand, zircon sand, olivine sand or the like. It is, of course, important to use a sand that is finely divided and that the sand be an inert sand.

The Reaction Conditions

Preferably the esterification reaction temperature of from 180° C. to 225° C. is controlled by the addition of an inert diluent of appropriate boiling point and/or by the use of sub-atmospheric pressure or by electronic temperature control.

Generally, in order to take the esterification reaction to completion the amount of alcohol used should be in excess of the stoichiometric amount required to react completely with the acid or acid anhydride. The water of reaction should be removed as an azeotrope with excess alcohol, which may be separated and returned to the reaction. Up to a 50% stoichiometric excess, of alcohol, preferably from 10% to 30% stoichiometric excess may be employed. Alternatively or in addition the water of reaction may be removed by the addition of an entrainer which may suitably be a hydrocarbon diluent or subsurface addition of $N_2$ gas.

Upon completion of the esterification reaction any unconverted alcohol present in the ester product may be removed by steam-stripping. Alcohol collected in this manner is preferably concentrated and recycled to the next reaction.

It is preferred to neutralize any residual acidity in the ester product and to remove any esterification catalyst present. This may suitably be achieved by the addition of an inorganic strong base, such as sodium carbonate or lime, which may be added either in the form of a solid or as an aqueous solution. Procedures and conditions for carrying out this step are well-known in the art and typically involve the use of an elevated temperature.

The steps of alcohol stripping and neutralization/catalyst removal are preferably effected outside the reactor in which the esterification process is carried out because the conditions and/or reagents employed may have a detrimental effect on the catalyst. It is therefore preferred to carry out the esterification process in a batch reactor and effect the operations on the ester product batchwise in a separate vessel. The batch reactor in which the esterification process is carried out may be fabricated in any suitable material such as stainless steel, titanium or glass, preferably, stainless steel.

The esterification process of the invention is particularly applicable to the production of plasticizers for use in the plastics industry from, for example, phthalic anhydride and a $C_4$ to $C_{14}$ alkanol or mixture of such alkanols, such as, for example, dibutyl phthalate or dioctyl phthalate, and it is also useful in the production of synthetic lubricant esters.

Throughout this application, all temperatures and degrees Celsius, and all parts and percentages are by weight, dry basis (i.e., $H_2O$-free), unless otherwise expressly specified. Pressures in microns (micrometers) are absolute pressures reported in metric units and referring to the height of a column of mercury supported by the pressure at which the reaction is conducted, where atmospheric pressure corresponds to 760 mm of mercury.

The invention will now be demonstrated by reference to the following Examples:

THE EXAMPLES

In the examples, equipment known to those skilled in the art was used. The equipment used included a glass batch reactor, means to lower the pressure in the reactor to thereby control the temperature of the contents of the reactor; means whereby some water of reaction is removed in a decanter operation whereby the decanter in the examples has been preloaded with 2-ethyl hexanol, and means whereby some water of reaction was also removed by the addition of $N_2$ gas into the subsurface of the reaction mix.

In the examples, the following products were used. 2-ethyl hexanol was obtained from Eastman Chemical Products, Inc. of Kingport, Tenn. and was identified as being at least 99.50% pure. The adipic acid used was identified as 99.8% pure. The sodium aluminate used was obtained from the United States Aluminate Company of Baltimore, Md. It was a white, hydroscopic powder identified as GU-55. According to the product bulletin GU-55 is essentially pure sodium aluminate containing a maximum of 0.2% insoluble matter and a maximum of 200 ppm of iron, Fe. GU-55 is labelled as containing 53.0–55.0% alumina ($Al_2O_3$). The formula of the GU-55 sodium aluminate is $Na_2Al_2O_4$. The sand was obtained from the Eastech Chemical, Inc., Philadelphia, Pa. and was identified as Sil co sil 63 and Sil co sil 75. According to the supplier, the sand had a median particle size in the range from 14–18 microns (Sedigraph 50% Paint ASTMC-958) and an average particle size in the range from 5.5–6.7 microns (Fisher Subsieve ASTMB-330). The sand was also identified as having sizes in the range of 200 mesh to 230 mesh.

In the examples, all parts and percentages are by weight unless otherwise noted.

EXAMPLE 1

PRODUCTION OF DIOCTYL ADIPATE BY REACTION OF 2-ETHYL HEXANOL AND ADIPIC ACID IN THE PRESENCE OF A CATALYST CONSISTING OF 92 PARTS SAND, 5 PARTS STANNOUS OXALATE, AND 3 PARTS SODIUM ALUMINATE, DRY BASIS

Preparation of A Mix of Sand and Stannous Oxalate

First, a mix was prepared by mixing together 92 parts by weight of clean, dry silica sand and 5 parts by weight of stannous oxalate.

Preparation of Sodium Aluminate Solution

Second, 2.5 parts by weight sodium aluminate ($Na_2Al_2O_4$) was dissolved in 97.5 parts by weight distilled water to make a 2.5% sodium aluminate solution.

Preparation Of Dioctyl Adipate In A Batch Reactor 897 grams (6.9 moles) of 2-ethyl hexanol (a liquid) were added to an empty standard glass reactor equipped with an agitator. 1.70 grams of the mix of sand and stannous oxalate ($4.11 \times 10^{-4}$ moles of stannous oxalate) and 0.34 grams of the sodium aluminate solution ($5.19 \times 10^{-5}$ moles of $Na_2Al_2O_4$) were added and agitated to mix well.

438 grams of adipic acid (3 moles) were added. At this point, applicants made sure the reactor was properly set up to include nitrogen purge means and decanter means, and that the decanter had been preloaded with 2-ethyl hexanol. The reactor was then closed and the nitrogen sparge or purge was set at a rate of 1–3 ml per minute. Heating up to 170° C. was started. The water of reaction was collected at about 150° C.–160° C. in the decanter. When the temperature inside the reactor reached 225° C., the pressure inside the reactor was measured in the range of 15–20 inches of mercury and at this point, the reactor was opened and the contents analyzed. The contents had esterified to an Acid Number of 0.032 (i.e. 0.032 mg of Mg/KOH/gm). The contents were then stripped of excess alcohol under high vacuum to an alcohol content of less than 0.1%. The contents were then cooled to 130° C., and filtered using activated carbon and filter aid to eliminate solids such as sand.

Measurement Of The Effectiveness Of The Esterification Reaction

After the reaction was completed, and the product was stripped, cooled and filtered, the product was analyzed and the following properties were noted:

| Appearance | Clear water white liquid |
|---|---|
| Color, APHA[1] | 10 |
| Purity as ester content, % | 99.8 |
| Acid Number Mg/Koh/gm | 0.32 |
| Hydroxyl Number | 0.40 |
| Refractive Index, @ 23° C. | 1.4460–1.4480 |
| Specific gravity, @ 23° C. | 0.924–0.928 |
| Flash point, °C. | 208 |

[1]American Public Health Association Standard

CONTROL EXAMPLE 2

Determining the Relative Usefulness of a Catalyst

In order to determine the usefulness of the catalysts of the invention, five control experiments were performed using as the catalyst for each of the controls one of the following, wherein in each case about 1.70 grams of control catalyst (dry basis) are used.

1. Sand without any active ingredient
2. Sand with 5 parts stannous oxalate
3. Sand with 3 parts sodium aluminate, $Na_2Al_2O_4$:
4. Sand with 8 parts stannous oxalate
5. Sand with 8 parts sodium aluminate, $Na_2Al_2O_4$:

In the control tests, the same equipment, the same amount of 2-ethyl hexanol and the same amount of adipic acid were used as in Example 1. The procedures followed were the same as those described in Example 1. As in Example 1, the reaction was terminated when the contents reached 225° C.

After completion of each test, the reactor was opened and the contents analyzed. The results of the analysis are set forth in Table I.

TABLE 1

Qualitative Comparison of the Reaction of 2-Ethyl Hexanol and Adipic Acid Using Catalyst of Invention (Example 1) With The Reaction Using Control Catalyst

| Control Catalyst Control # | Composition By Weight | | | Use Of Control Catalyst As Compared With Use Of Catalyst of The Invention |
|---|---|---|---|---|
| | Sand | Stannous Oxalate | Sodium Aluminate | |
| 1. | 100% | — | — | reaction was not complete |
| 2. | 97% | 5% | — | reaction was very slow |
| 3. | 97% | — | 3% | reaction was very slow |
| 4. | 92% | 8% | — | reaction was slow and product was discolored |
| 5. | 92% | — | 8% | reaction was slow |

The catalyst of Example 1 as compared with the control catalysts provided a faster reaction and provided for the making of an ester product with good color stability (i.e. was not discolored) and almost negligible acidity, thereby eliminating the need for a wash process.

Determining How Much Active Ingredient Can Be Used In Making An Acceptable Catalyst Of The Invention Applicants believe that the combination of sodium aluminate and stannous oxalate acts as the catalyst, that the sand is the carrier for the catalyst, and that the water is the ionizing agent for the sodium aluminate. Sand concentration may vary from 1% to 90% of the total weight of the catalyst mixture. Usually, the weight amount of the catalyst mixture, which includes the sand, that is used is equal to a weight amount of about 0.12% based on the total reactor loadings, i.e., the reaction mixture.

Example 1 was conducted using 0.153% of the catalyst based on the total reactor loadings. The catalyst was composed of 92% sand, 5% stannous oxalate, and 3% sodium aluminate. However, other tests were run to determine the relative usefulness of catalyst as follows.

Other Examples

Demonstrations of the invention, making dioctyl adipate, were performed as described in Example 1, using catalysts of the invention containing different proportions of the three ingredients. The results of these demonstrations are set forth as follows.

1. When the catalyst was: 5% sand, 90% stannous oxalate and 5% sodium aluminate dry basis dissolved in distilled water; the reaction results were good.
2. When the catalyst was: 92% clean, dry silica sand, 5% stannous oxalate; and 25% sodium aluminate, dry basis, dissolved in distilled water; the reaction results were good.
3. When the catalyst was: 97% clean, dry silica sand; 2% stannous oxalate; and 1% sodium aluminate, dry basis, dissolved in distilled water; the reaction rate was quite slow.
4. When the catalyst was: 50% clean, dry silica sand; 25% stannous oxalate; and 25% sodium aluminate, dry basis, dissolved in distilled water; the reaction rate was acceptable, but the product was high in color (discolored).

Conclusions

As a result of the experiments carried out to make dioctyl adipate from 2-ethyl hexanol and adipic acid according to the procedures set forth in Example 1, it has been clearly demonstrated that dioctyl adipate can be made at commercially viable production rates and at temperatures low enough to produce commercially acceptable products using a catalyst composed of tin salt, aluminum compound and sand.

In the above examples, it was demonstrated that a preferred catalyst of the invention consists of: 92 parts clean dry silica sand; 5 parts stannous oxalate; and 3 parts sodium aluminate, dry basis.

It was also demonstrated that another preferred catalyst consists of 92 parts sand, 5 parts stannous oxalate and 25 parts sodium aluminate. It may therefore be concluded that catalysts having a sodium aluminate to stannous oxalate ratios of 5:3 and 5:25 are acceptable.

It is further demonstrated that two unacceptable catalysts had sodium aluminate to stannous oxalate ratios of 1:2 and 1:1.

While the demonstrations of the invention have related to the production of dioctyl adipate, fast reaction rates, good yields, and products of good properties, color, and purity, are generally obtained or may be obtained by experimental optimization of the reaction conditions, to produce esters from the specific reactant and from the classes of reactants already mentioned.

While the reaction catalyst operates well, it is theorized that in the aqueous reaction environment, the alkali metal aluminate and the stannous oxalate provide stannous ions and aluminate ions that together provide the active catalyst, possibly through the formation of stannous aluminate.

While the invention has been disclosed in this patent application by reference to the details of preferred embodiments of the invention, it is to be understood that the disclosure is intended in an illustrative rather than a limiting sense, as it is contemplated that modifications may readily occur to those skilled in the art, within the spirit of the invention and the scope of the appended claims.

What is claimed is:

1. A process for the production of esters boiling above 100° C. which comprises reacting an alcohol component with an organic acid or anhydride component, at a temperature greater than 100° C., in the presence of an esterification catalyst composition wherein said catalyst composition consists essentially of:

(1) sand;
   (2) a source of stannous tin; and
   (3) an aluminate wherein said catalyst composition in the presence of water forms stannous and aluminate ions; wherein said source of stannous tin is selected from the group consisting of stannous acetate, stannous tartrate, stannous benzoate, stannous citrate, stannous oxalate, stannous phthalate, stannous sebacate, stannous formate, stannous octoate, dibutyl tin oxide and mixtures thereof; wherein said aluminate is selected from the group consisting of sodium aluminate, potassium aluminate, magnesium aluminate, cesium aluminate, and mixtures thereof; and wherein said sand has particle sizes predominantly in the range of from about 5 microns to about 18 microns in diameter.

2. The process of claim 1 wherein said catalyst composition consists essentially of 95 parts sand, 5 parts stannous oxalate and 3 parts sodium aluminate.

3. The process of claim 1 wherein said catalyst composition consists essentially of about 92% by weight sand and about 5% by weight of stannous oxalate, and about 3% by weight of sodium aluminate.

4. The process of claim 1 wherein said alcohol component is selected from the group consisting of monohydric alcohols and dihydric alcohols, and wherein said organic acid component is selected from the group consisting of monobasic and polybasic carboxylic acids.

5. The process of claim 1 wherein said acid component is selected from the group consisting of dibasic acid anhydrides.

6. The process of claim 1 wherein said source of aluminate is sodium aluminate and said source of stannous tin is stannous oxalate and wherein the weight ratio of sodium aluminate to stannous oxalate is in the range from 5:3 through 5:25.

7. The process of claim 6 wherein said composition consists essentially of about 5% sand, about 90% stannous oxalate and about 5% sodium aluminate.

* * * * *